United States Patent
Walton et al.

(10) Patent No.: US 6,479,154 B1
(45) Date of Patent: Nov. 12, 2002

(54) COEXTRUDED, ELASTOMERIC BREATHABLE FILMS, PROCESS FOR MAKING SAME AND ARTICLES MADE THEREFROM

(75) Inventors: Glynis Allicia Walton; Susan Elaine Shawver, both of Roswell; James Russell Fitts, Jr., Gainesville, all of GA (US); Jennifer Rebecca Reavis, Edison, NJ (US); Richard Macferran Shane, Lilburn, GA (US); Duane Girard Uitenbroek, Gainesville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/696,560

(22) Filed: Oct. 25, 2000

Related U.S. Application Data

(60) Provisional application No. 60/162,657, filed on Nov. 1, 1999.

(51) Int. Cl.[7] .................................. B32B 27/00
(52) U.S. Cl. .................. 428/424.4; 428/424.8; 428/474.4; 428/516; 428/520
(58) Field of Search ............... 428/424.8, 424.4, 428/516, 474.4, 520

(56) References Cited

U.S. PATENT DOCUMENTS

| | | | |
|---|---|---|---|
| 3,046,172 A | 7/1962 | Reid | 154/46 |
| 3,338,992 A | 8/1967 | Kinney | 264/24 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,844,865 A | 10/1974 | Elton et al. | 156/229 |
| 3,849,241 A | 11/1974 | Butin et al. | 161/169 |
| 3,855,046 A | 12/1974 | Hansen et al. | 161/150 |
| 4,041,203 A | 8/1977 | Brock et al. | 428/157 |
| 4,265,960 A | 5/1981 | Arbit et al. | 428/220 |
| 4,340,563 A | 7/1982 | Appel et al. | 264/518 |
| 4,364,985 A | 12/1982 | Tokuyama et al. | 428/149 |
| 4,374,888 A | 2/1983 | Bornslaeger | 428/198 |
| 4,443,513 A | 4/1984 | Meitner et al. | 422/195 |
| 4,472,328 A | 9/1984 | Sugimoto et al. | 264/41 |
| 4,522,203 A | 6/1985 | Mays | 128/132 |
| 4,533,510 A | 8/1985 | Nissel | 264/171 |
| 4,663,220 A | 5/1987 | Wisneski et al. | 428/221 |

(List continued on next page.)

FOREIGN PATENT DOCUMENTS

| WO | 96/19346 A3 | 6/1996 | |
|---|---|---|---|
| WO | WO 96/19346 A2 * | 6/1996 | ............ B32B/7/00 |
| WO | 97/04955 A1 | 2/1997 | |
| WO | 98/23804 A1 | 6/1998 | |
| WO | 98/29480 | 7/1998 | |
| WO | 98/58799 | 12/1998 | |
| WO | 99/14044 A1 | 3/1999 | |
| WO | 99/14262 A1 | 3/1999 | |

OTHER PUBLICATIONS

Japan J6 3286–439–A, Abstract, Nov. 24, 1988, Nippon Magfan KK; 1989 Derwent Publications Ltd.

(List continued on next page.)

Primary Examiner—James J. Seidleck
Assistant Examiner—Melanie Bissett
(74) Attorney, Agent, or Firm—Steven D. Flack

(57) ABSTRACT

A breathable, elastic multilayered film including a core layer of a first elastomer and at least one filler and at least one skin layer of a second elastomer; wherein the first elastomer is a polyolefin and the second elastomer is selected from the group consisting of thermoplastic polyurethanes, polyetheramides, block copolymers, and combinations thereof. Alternatively, at least one support layer may be bonded to the multilayered film.

11 Claims, 2 Drawing Sheets

U.S. PATENT DOCUMENTS

| | | | |
|---|---|---|---|
| 4,720,415 A | 1/1988 | Wielen et al. | 428/152 |
| 4,734,324 A | 3/1988 | Hill | 428/317.3 |
| 4,758,239 A | 7/1988 | Yeo et al. | 604/366 |
| 4,777,073 A | 10/1988 | Sheth | 428/155 |
| 4,789,699 A | 12/1988 | Kieffer et al. | 524/271 |
| 4,795,668 A | 1/1989 | Krueger et al. | 428/174 |
| 4,923,650 A | 5/1990 | Antoon, Jr. et al. | 264/41 |
| 4,965,122 A | 10/1990 | Morman | 428/225 |
| 5,011,698 A | 4/1991 | Antoon, Jr. et al. | 426/395 |
| 5,057,368 A | 10/1991 | Largman et al. | 428/397 |
| 5,064,802 A | 11/1991 | Stevens et al. | 502/155 |
| 5,069,970 A | 12/1991 | Largman et al. | 428/373 |
| 5,108,820 A | 4/1992 | Kaneko et al. | 428/198 |
| 5,116,662 A | 5/1992 | Morman | 428/198 |
| 5,164,258 A | 11/1992 | Shida et al. | 428/319.3 |
| 5,176,953 A | 1/1993 | Jacoby et al. | 428/315.5 |
| 5,178,931 A | 1/1993 | Perkins et al. | 428/198 |
| 5,188,885 A | 2/1993 | Timmons et al. | 428/198 |
| 5,204,429 A | 4/1993 | Kaminsky et al. | 526/308 |
| 5,271,883 A | 12/1993 | Timmons et al. | 264/6 |
| 5,277,976 A | 1/1994 | Hogle et al. | 428/397 |
| 5,288,791 A | 2/1994 | Collier~IV et al. | 524/505 |
| 5,332,613 A | 7/1994 | Taylor et al. | 428/152 |
| 5,336,545 A | 8/1994 | Morman | 428/152 |
| 5,336,552 A | 8/1994 | Strack et al. | 428/224 |
| 5,374,696 A | 12/1994 | Rosen et al. | 526/126 |
| 5,382,400 A | 1/1995 | Pike et al. | 264/168 |
| 5,393,599 A * | 2/1995 | Quantrille et al. | 428/284 |
| 5,451,450 A | 9/1995 | Erderly et al. | 428/220 |
| 5,466,410 A | 11/1995 | Hills | 264/172.11 |
| 5,472,775 A | 12/1995 | Objeski et al. | 428/220 |
| 5,489,469 A | 2/1996 | Kobayashi et al. | 428/283 |
| 5,539,124 A | 7/1996 | Etherton et al. | 548/402 |
| 5,540,976 A | 7/1996 | Shawver | 428/198 |
| 5,540,992 A | 7/1996 | Marcher et al. | 428/373 |
| 5,554,775 A | 9/1996 | Krishnamurti et al. | 556/7 |
| 5,599,420 A | 2/1997 | Yeo et al. | 156/290 |
| 5,650,225 A | 7/1997 | Dutta et al. | 428/318.4 |
| 5,691,034 A | 11/1997 | Krueger et al. | 428/152 |
| 5,695,868 A | 12/1997 | McCormack | 428/283 |
| 5,723,546 A | 3/1998 | Sustic | 525/240 |
| 5,733,628 A | 3/1998 | Pelkie | 428/138 |
| 5,759,926 A | 6/1998 | Pike et al. | 442/333 |
| 5,910,136 A | 6/1999 | Hetzler et al. | 604/367 |
| 5,984,911 A | 11/1999 | Siebers et al. | 604/391 |

OTHER PUBLICATIONS

BF Goodrich Specialty Chemicals, Product Data Sheet, "Estane®Thermoplastic Polyurethane: 'Rubber–like' Thermoplastic Polyurethanes", Dec. 1994.

BF Goodrich Specialty Chemicals, Product Data Sheet, "Estane®58237 Thermoplastic Polyurethane: Polyether Based Polyurethane", Dec. 1996.

BF Goodrich Specialty Chemicals, Product Data Sheet, "Estane®58238 Thermoplastic Polyurethane: Thermoplastic Polyurethane Compound", Aug. 1994.

BF Goodrich Specialty Chemicals, Product Data Sheet, "Estane®58245 Thermoplastic Polyurethane: Polyetherthane Based Polyure", Dec. 1996.

BF Goodrich Specialty Chemicals, Product Data Sheet, "Estane®58661 Thermoplastic Polyurethane: Thermoplastic Polyurethane Compound", Aug. 1994.

DeGaspari, J., "New TPEs Push Performance Envelope", *Plastics Technology*, Nov. 1997.

DuPont®, "Hytrel® Polyester Elastomer Product Data Sheets", Jul. 1997.

Elf Atochem North America, Inc. Technical Information Sheet, "PEBAX® Resins Tech Facts: Preliminary Data Sheet of Typical Physical Properties of Hydrophilic PEBAX® Grades", Jan. 1993.

Elf Atochem North America, Inc., Technical Information Sheet, "PEBAX® Resins: 33 Series Property Comparison", May 1994.

Elf Atochem North America, Inc., Technical Information Sheets, "PEBAX® MV 6200 SN 01".

Elf Atochem North America, Inc., Technical Information Sheets, "Preliminary Data for PEBAX® MV3000 SN01".

Elf Atochem S.A, Product Description, "PEBAX® 0 Breathable Films: Polyether Block Amides", Jan. 1992.

The Dow Chemical Company, "Pellethane Thermoplastic Polyurethane Elastomers", 306–00183/1 pp. 3–7; 306–00434/1 pp. 20–23, Jul. 1997.

* cited by examiner

COEXTRUDED, ELASTOMERIC BREATHABLE FILMS, PROCESS FOR MAKING SAME AND ARTICLES MADE THEREFROM

This application claims priority from U.S. Provisional Application No. 60/162,657 filed on Nov. 1, 1999.

FIELD OF THE INVENTION

The present invention relates to coextruded elastomeric breathable films for use in conformable garments and personal care products. More particularly, the present invention relates to multilayered films and film laminates for use with fabrics in disposable garments and personal care products.

BACKGROUND OF THE INVENTION

The present invention is directed to thin multilayer films and their use in laminates and articles made therefrom. Film laminates have become an important article of commerce, finding a wide variety of applications, including use within various articles; for example, as outer covers for personal care products such as diapers, training pants, incontinence garments, feminine hygiene products and the like. In addition, film laminates have found use in various other bodily articles such as garments, surgical gowns, protective workwear, wound dressings, bandages and the like. The film can provide the desired barrier properties to the article while other materials laminated thereto can provide additional desired characteristics, such as abrasion resistance and/or good hand. In addition, in order to increase the comfort of the wearer, film laminates have been desirably "breathable", in the sense that the laminates act as a barrier to liquids, but allow water vapor and air to pass therethrough. By achieving and maintaining high breathability, it is possible to provide an article that is more comfortable to wear since the migration of water vapor through the fabric helps reduce and/or limit discomfort from excess moisture trapped against the skin. Thus, such an article can potentially contribute to an overall improved skin wellness. Therefore, it is often desirable to use a film to achieve desired comfort levels in an article. To this end, films have been engineered to achieve specific desired objectives.

For instance, while a variety of film laminates are known in the art, one particularly useful laminate uses a breathable barrier comprising a stretched filled multilayered (as opposed to a monolayer) microporous film. Such films are typically comprised of a relatively thick and often more expensive core layer, encompassing the majority of the film material, and relatively thinner outer skin layers. The core layer is often filled with particles or other matter and then crushed or stretched to form a fine pore network throughout the layer. The pores result from the separation of the polymer from the filler particles. The film-pore network allows relatively high levels of gas and water vapor to pass through the film while acting as a barrier to liquids and particulate matter. The amount of filler within the film and the degree of stretching is controlled so as to create a network of micropores of a size and/or frequency to impart the desired level of breathability to the fabric.

An exemplary stretched filled-film is described in commonly assigned WO Patent Application 96/19346 to McCormack which discloses a multilayered filled-film comprising a breathable microporous core layer made from an extrudable thermoplastic polymer such as a polyolefin, including copolymers and/or blends thereof. One or more breathable microporous skin layers are attached to the core layer. McCormack emphasizes use of a generic type core layer and specifically designed skin layers. The described skin layers include extrudable thermoplastic polymers and/or additives designed to impart specialized properties to the overall film. The selection of skin layer polymers in the McCormack reference depends on the overall film attributes desired. Possible skin layer polymers are described, including homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon, ethylene vinyl alcohol (EVOH), polystyrene, polyurethane and olefinic thermoplastic elastomers. Additionally, McCormack describes the use of anti-block material to improve processing and/or to prevent unwanted adhesion of layers. The particulate filled-film of McCormack can be stretched to impart breathability. The stretched film may then be laminated to a nonwoven web to create a laminate that takes advantage of the strength and integrity of the nonwoven web and the barrier properties of the stretched film. The McCormack reference does not provide for the use of higher performance elastomers, while still providing a relatively high level of breathability at low cost.

Films have also been designed with skin layers that specifically help to reduce the occurrence of die lip buildup, that is the residual buildup of filler particles which tend to accumulate on an extruder die as the filled polymer is extruded during the film manufacturing process. This buildup of material on the die lip slows the manufacturing process since it requires the process to be stopped in order for the die lip to be scraped clean of the excess material. Such skin layers including EVA, are often used in order to reduce this accumulation of the filler particles.

Commonly assigned WO Patent Application 99/14262 to Shawver et al. describes a breathable microporous film comprised of a thermoplastic polymer blend of a first polyethylene polymer having a density below 0.89 g/cm$^3$, a second polyethylene polymer having a density above about 0.90 g/cm$^3$, and a filler. In particular, the reference describes the use of a single site/metallocene catalyzed polyethylene as a film component. While the attributes of this film are described as providing good breathability and body conformance, as well as not suffering from shrinkage when exposed to heat, the Shawver reference does not describe strategically placed higher cost elastomeric materials to help buttress the elastomeric properties of lower cost elastomers in a film, nor the use of higher performance elastomers while still achieving relatively high levels of breathability. Although such films demonstrate elastic properties, a film having better elastic properties than that of metallocene catalyzed polyethylene elastomers is desirable.

In addition to breathability of the multilayered film laminate, the ability of the laminate to exhibit higher performance elastic properties allows a garment made therefrom to provide better body conformance. However, providing a low cost multilayered laminate that achieves the desired conformance and breathability is problematic, particularly with stretched filled-films. In order to achieve good body conformance, the polymer composition of the film layers desirably should have good stretch and recovery properties and yet must also be capable of allowing formation and retention of pores upon processing. These two objectives are often at odds with each other.

For instance, U.S. Pat. No. 5,691,034 to Krueger et al. describes a multilayered elastomeric laminate with microtextured skin layers. The multilayered laminate is comprised of at least one elastomeric layer and at least one thin skin layer prepared by coextrusion. The laminate is illustrated in the patent as having three layers. Following coextrusion, the laminate is stretched past the elastic limit of the skin layers and allowed to recover. While the Krueger reference provides for the use of costly high performance elastomeric materials, it does not provide for breathability in the described laminate. This is particularly difficult to achieve using higher performance elastomers since these elastomers also lead to pore closure following stretching. Essentially, because of the retraction properties of the elastomer materials, the micropores necessary to make the film breathable do not always remain open after the stretching process.

One solution to this problem has been to add additional filler to reduce the tendency for the material to retract, thus allowing more micropores to remain open, thereby producing a breathable product. However, this decrease in the retraction attribute produces a higher percent set in the final product, that is generally a percent of elongation following stretch, resulting in a loss of fit or sagging over time when used in an article that will encounter movement (also known as dampening).

It is also known to use five layers in a multilayered film to achieve a breathable film. Such films often require tie or adhesive layers to bind the various skin/outer layers to a central core layer. It has been found that the use of an adhesive component in the core layer leads to manufacturing difficulties as the tackifier often promotes unwanted sticking/adhesion during the film manufacturing process. A five layered film structure is disclosed in U.S. Pat. No. 5,164,258 to Shida et al. Shida discloses a multilayered structure having a monolithic film core layer of a hygroscopic gas barrier and inner and outer surface layers engineered to facilitate the escape of moisture which becomes absorbed in the core. The outer layers are described as either foamed or filled, in order to increase their water vapor transmission rate (WVTR). Shida et al. does not describe elastic attributes of the multilayered films.

Furthermore, three and five layer films are described in commonly assigned WO Patent Application 97/04955 to Forte. Forte describes a multilayered breathable film and a method for making such a film. The five layered film, which is preferred over a described three layer embodiment, includes two adhesive, microporous layers to facilitate bonding of the various layers. The outer layers are monolithic and the microporous core layer is filled to achieve a desired level of breathability, or WVTR. In describing five layer films having adhesive layers, the Forte reference discloses a core layer that includes a thermoplastic polymer containing a metallocene catalyzed polyethylene. Forte also describes the outer monolithic skin layers as comprising a hydrophilic polymeric resin. In particular, Forte describes the use of certain resins, and in particular Pebax® brand polymeric resins in the outer five layers, specifically Pebax®4033 resin.

The three layered films described in the Forte reference utilize a microporous and adhesive core layer, with the adhesive component comprised of either polymeric materials capable of bonding to the layers, a mixture of materials from the outer monolithic layer, or scraps of multilayered films. The three layered embodiment described in this patent does not include a separate outer adhesive layer but makes use of an EMA material melt blended in the noncompatible skin layer to promote compatibility between the skin and core layer materials.

While Forte describes microporous multilayered films which are elastomeric, Forte does not describe a multilayered film which strategically places higher performance elastomeric materials in various positions in the film composite in order to buttress lower performance, lower cost elastomeric materials, and which are particularly effective at a certain stretch, and also does not describe "product" films of relatively high breathability, which are themselves capable of specific additional stretch and recovery attributes, especially for the three layered film embodiment.

Thus, there exists a need for an efficient film and laminate thereof which is capable of providing relatively high breathability (i.e. WVTR) and body conformance, with the use of mainly lower cost elastomers, but including higher cost, high performance elastomers strategically placed in a film composite to buttress the performance of the relatively low performance elastomers, and without sacrificing breathability. There exists a need for a product multilayer film and film laminate which themselves demonstrate the attributes of stretch with significant recovery or retraction. Such an improvement would benefit the maintenance of fit of an article produced from such films and/or laminates. There exists a need for a multilayered elastic and breathable film with reduced die lip buildup during manufacture and which includes a compatibilizer to allow for the coextrusion of both polar and non-polar materials. Further there exists a need for a three layered film which is both elastic and breathable and yet does not suffer from the logistical complications of manufacturing a five layered film.

SUMMARY OF THE INVENTION

The aforesaid needs are fulfilled and the problems experienced by those skilled in the art overcome by the multi-layered film of the present invention, which includes a filled core layer of a first elastomer, a primarily relatively low cost, low performance elastomer, and at least one monolithic skin layer of a second elastomer, a higher performance elastomer to help buttress the elastomeric attributes of the core layer. The filled-film is stretched/oriented to create a microporous film having voids adjacent to the filler wherein the film has a WVTR of at least 1,000 $g/m^2/24$ hours. The resulting microporous film of the present invention demonstrates elasticity without sacrificing breathability. Desirably, the core layer is comprised of a less costly, low performance elastomer having a hysteresis value greater than about 75 percent such as a polyolefin elastomer, and in particular elastomeric metallocene-catalyzed polyethylene. Alternatively, small amounts of higher performance elastomer, such as a styrenic block copolymer (such as a Kraton® G) may be blended with the lower performance-lower cost elastomer in the core to improve the overall elastic performance of the material.

Desirably, the skin layers are comprised of blended higher performance elastomers, and in particular thermoplastic polyurethane elastomers and polyetheramides having a hysteresis value of less than about 75 percent and desirably less than 60 percent. Desirably, EMA with high methyl acrylate levels is blended with the higher performance elastomer in the skin layers to act as a compatibilizer and improve adhesion to the core layer and fibrous outer layer in a laminate. The skin layer aids in reducing die lip buildup during the film extrusion process.

In a further aspect of the invention, a styrenic block copolymer elastomeric resin is added to the elastic skin layer(s) to act as a compatibilizer to assist in the adhesion of two incompatible materials, such as those found in the core and skin layers.

In still a further aspect of the invention, the microporous film of the present invention is laminated to a fibrous layer. The fibrous layer can be a nonwoven web such as, for example, an extensible nonwoven web. Film nonwoven laminates of the present invention can be used as a barrier layer in bodily articles such as, for example, in diapers as outer covers, adult incontinence garments, protective apparel and the like. Additionally, and in still a further aspect of the present invention, the breathable microporous films and/or film laminates of the present invention make up a component of an absorbent bodily article. As one example, an absorbent bodily article can include a liquid pervious liner; an absorbent core; and a microporous film or film laminate of the present invention wherein the absorbent core is positioned between the liquid pervious liner and microporous film or film laminate.

DEFINITIONS

Figure 1:
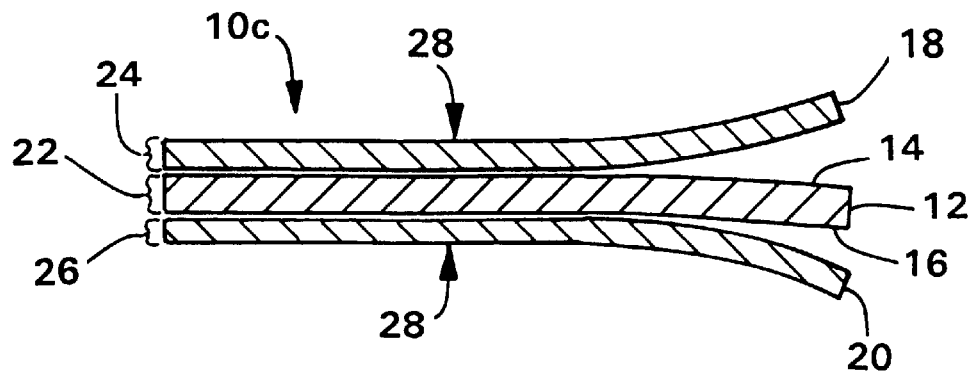
FIG. 1 is a cross-sectional side view, of a multilayer product film according to the present invention. The right side of the film has been split apart to facilitate its description.

As used herein and in the claims, the term "comprising" is inclusive or open-ended and does not exclude additional unrecited elements, compositional components, or method steps.

As used herein the term "recover" refers to a contraction of a stretched material upon termination of a biasing force following stretching of the material by application of the biasing force. For example, if a material having a relaxed, unbiased length of 1 inch (2.5 cm) is elongated fifty percent by stretching to a length of 1.5 inches (3.75 cm), the material would be elongated 50 percent and would have a stretched length that is 150 percent of its relaxed length or stretched 1.5×. If this exemplary stretched material contracted, that is recovered to a length of 1.1 inches (2.75 cm) after release of the biasing and stretching force, the material would have recovered 80 percent of its 0.5 inch (1.25 cm) elongation. Percent recovery may be expressed as [(maximum stretch length-final sample length)/(maximum stretch length—initial sample length)]×100.

As used herein the term "nonwoven" fabric or web means a web having a structure of individual fibers or threads which are interlaid, but not in an identifiable manner as in a knitted fabric. Nonwoven fabrics or webs have been formed by many processes such as for example, meltblowing processes, spunbonding processes, hydroentangling, air-laid and bonded carded web processes.

As used herein the term "extensible" means elongatable or stretchable in at least one direction.

As used herein the term "spunbond fibers" refers to small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. each being incorporated by reference in its entirety. Spunbond fibers are generally not tacky when they are deposited onto a collecting surface and are generally continuous. Spunbond fibers are often about 10 microns or greater in diameter. However, fine fiber spunbond webs (having an average fiber diameter less than about 10 microns) may be achieved by various methods including, but not limited to, those described in commonly assigned WO Patent Application. 98/23804 to Marmon et al. and U.S. Pat. No. 5,759,926 to Pike et al.

As used herein the term "meltblown fibers" means fibers of polymeric material which are generally formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter. Thereafter, the meltblown fibers can be carried by the high velocity gas stream and are deposited on a collecting surface to form a web of randomly dispersed meltblown fibers. Such a process is disclosed, for example, in U.S. Pat. No. 3,849,241 to Butin et al. and 5,271,883 to Timmons et al. each being incorporated by reference in its entirety. Meltblown fibers may be continuous or discontinuous, are generally smaller than 10 microns in average diameter, and are generally tacky when deposited onto a collecting surface.

As used herein "multilayer nonwoven laminate" means a laminate of two or more layers in which at least one of the layers is a nonwoven material such as, for instance, a spunbond layer. For example, a multilayer nonwoven laminate may include a spunbond/meltblown/spunbond (SMS) laminate, or a laminate in which at least one of the layers is a nonwoven and the other layer(s) is another material such as a film in a spunbond/film laminate (SF). Examples of multilayer nonwoven laminates are disclosed in U.S. Pat. No. 4,041,203 to Brock et al., U.S. Pat. No. 5,178,931 to Perkins et al. and U.S. Pat. No. 5,188,885 to Timmons et al. each being incorporated by reference in its entirety. Such a laminate may be made by sequentially depositing onto a moving forming belt first a spunbond fabric layer, then a meltblown fabric layer and last another spunbond layer and then bonding the laminate such as by thermal point bonding as described below. Alternatively, the fabric layers may be made individually, collected in rolls, and combined in a separate bonding step.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible spacial configurations of the molecule. These configurations include, but are not limited to isotactic, syndiotactic and random symmetries.

As used herein, the term "machine direction" or MD means the length of a fabric in the direction in which it is produced. The term "cross machine direction" or CD means the width of fabric, i.e. a direction generally perpendicular to the MD.

As used herein, "ultrasonic bonding" means a process performed, for example, by passing the fabric between a sonic horn and anvil roll as illustrated in U.S. Pat. No. 4,374,888 to Bomslaeger.

As used herein "point bonding" means bonding one or more layers of fabric at a plurality of discrete bond points. For example, thermal point bonding generally involves passing one or more layers to be bonded between heated rolls such as, for example an engraved pattern roll and a smooth calender roll. The engraved roll is patterned in some way so that the entire fabric is not bonded over its entire surface, and the anvil roll is usually flat. As a result, various patterns for engraved rolls have been developed for functional as well as aesthetic reasons. One example of a point bond pattern is the Hansen Pennings or "H&P" pattern with about a 30 percent bond area when new and with about 200 bonds/square inch as taught in U.S. Pat. No. 3,855,046 to Hansen and Pennings, incorporated by reference herein in its entirety. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). Another typical point bonding pattern is the expanded Hansen Pennings or "EHP" bond pattern which produces a 15 percent bond area when new with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15 percent when new. Yet another common pattern is the C-Star pattern which has, when new, a bond area of about 16.9 percent. The C-Star pattern has a cross-directional bar or "corduroy" design interrupted by shooting stars. Other common patterns include a diamond pattern with repeating and slightly offset diamonds with about a 16 percent bond area and a wire weave pattern looking as the name suggests, e.g. like a window screen, with about a 15 percent bond area. A further pattern is the "s-weave" pattern having about a 17 percent bond area when new and a baby objects pattern having about a 12 percent bond area when new. Such bonding pattern is further described in U.S. Pat. No. 5,599,420 to Yeo et al., incorporated by reference herein in its entirety. Typically, the percent bonding area is less than about 50 percent and more desirably varies from around 10 percent to around 30 percent of the area of the fabric laminate web.

As used herein "elastic" or "elastomeric" refers to material which, upon application of a biasing force, is extensible or elongatable in at least one direction and returns approximately to its original dimensions after the force is removed. For example, an elongated material having a biased length which is at least 50 percent greater than its relaxed unbiased length, and which will recover to within at least 50 percent of its elongation upon release of the elongating force. A hypothetical example would be a one (1) inch sample of a material which is elongatable to at least 1.50 inches and which, upon release of the biasing force, will recover to a length of not more than 1.25 inches.

As used herein the term "percent stretch" refers to the ratio determined by measuring the increase in the stretched dimension and dividing that value by the original dimension. i.e. (increase in stretched dimension/original dimension)× 100.

As used herein the term "set" refers to retained elongation in a material sample following the elongation and recovery, i.e. after the material has been stretched and allowed to relax.

As used herein the term "percent set" is the measure of the amount of the material stretched from its original length after being cycled. The remaining strain after the removal of the applied stress is measured as the percent set. The percent set is where the retraction curve of a cycle crosses the elongation axis, and as further discussed below.

As used herein, the term "inelastic" or "nonelastic" refers to any material which does not fall within the definition of "elastic" above.

As used herein, the term "breathable" refers to a material which is permeable to water vapor having a minimum WVTR (water vapor transmission rate) of about 1,000 g/m$^2$/24 hours. The WVTR of a fabric, in one aspect, gives an indication of how comfortable a fabric would be to wear. WVTR is measured as indicated below and the results are reported in grams/square meter/24 hours. However, often applications of breathable barriers desirably have higher WVTRs and breathable barriers of the present invention can have WVTRs exceeding about 1,200 g/m$^2$/24 hours, 1,500 g/m$^2$/24 hours, 1,800 g/m$^2$/24 hours or even exceeding 2,000 g/m$^2$/24 hours.

As used herein the term "blend" means a mixture of two or more polymers. In some instances the components of the blend are not compatible but have been melt mixed under high shear to provide a homogeneous blend.

As used herein the term compatibilizer means a material which assists in the adhesion of two normally incompatible materials.

As used herein, the term "garment" means any type of apparel which may be worn. This includes industrial work wear and coveralls, undergarments, pants, shirts, jackets, gloves, socks, and the like.

As used herein, the term "personal care product" means diapers, training pants, absorbent underpants, adult incontinence products, and feminine hygiene products.

As used herein, the term "high performance elastomer" means an elastomer having a level of hysteresis of less than about 75 percent as determined by the method described below and desirably, less than about 60 percent for a sample at 10 gsm. The hysteresis value is determined by first elongating a sample to an ultimate elongation of a given percentage (such as 50 or 100 percent) and then allowing the sample to retract to an amount where the amount of resistance is zero. For the purposes of this application, the term ultimate elongation should be understood to mean a pre-defined elongation percentage. For the purposes of this application, the hysteresis value determining numbers as used in the definition of high and low performance elastomers, (and as further explained below) are read at the 30 percent and 50 percent total ultimate elongation in the cross-machine direction.

As used herein, the term "low performance elastomer" means an elastomer having a level of hysteresis of greater than about 75 percent, determined by the method described below.

As used herein, the term "precursor film" means a filled film which has not yet been stretched or oriented so as to separate its particulate filler from its polymer component to thereby produce micropores.

As used herein, the term "product film" means a microporous filled film which has been stretched or oriented so that voids have formed around its particulate filler components so as to separate its particulate filler from the polymer components. The product film may be used in this form or subsequently used in a laminate.

As used herein the term "monolithic" means an unfilled film or film layer.

As used herein, a "filler" is meant to include particulates and/or other forms of materials which can be added to a film polymer extrusion material which will not chemically interfere with or adversely affect the extruded film and further which are capable of being uniformly dispersed throughout the film. Generally the fillers will be in particulate form with average particle sizes in the range of about 0.1 to about 10 microns, desirably from about 0.1 to about 4 microns.

As used herein, the term "particle size" describes the largest dimension or length of the filler particle.

As used herein, the term "bicomponent fibers" refers to fibers which have been formed from at least two polymer sources extruded from separate extruders but spun together to form one fiber. Bicomponent fibers are also sometimes referred to as conjugate fibers or multicomponent fibers. The polymers are arranged in substantially constantly positioned distinct zones across the cross-sections of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger et al., U.S. Pat. No. 5,540,992 to Marcher et al., and U.S. Pat. No. 5,336,552 to Strack et al., each being incorporated by reference in its entirety. Bicomponent fibers are also taught by U.S. Pat. No. 5,382,400 to Pike et al. For two component fibers, the polymers may be present in ratios of 75/25, 50/50, 25/75 or any other desired ratio.

DETAILED DESCRIPTION OF THE INVENTION

The present invention is directed to multilayer breathable, elastomeric product films, that is, films having two or more layers, methods for making such films, as well as the films laminated to support layers such as, for example, fibrous nonwoven webs. Referring to FIG. 1, there is shown a multilayer product film (and in particular, a product film that has been removed from the manufacturing process) 10c, which, for purposes of illustration has been split apart at the right side of the drawing. The multilayer product film 10c includes a core layer 12. The core layer 12 has a first exterior surface 14 and a second exterior surface 16. The core layer also has a core thickness 22. Attached to the first exterior surface 14 of the core layer 12 is a first skin layer 18 which has a first skin thickness 24. Attached to the second exterior surface 16 of the core layer 12 is an optional second skin layer 20 which has a second skin thickness 26. Desirably, the multilayered film has three layers.

The core layer 12, which desirably makes up between about 85 and 98 percent of the overall film, is made from a first elastomer, an extrudable low performance elastomeric polymer or a mixture of said polymers, such as polyolefins. The core layer is desirably comprised of polyethylene, and in particular, single site/metallocene-catalyzed polyethylene available under the trade names Dow Engage® EG8200 and Dow Affinity ® PL 1845 of the Dow Chemical Company.

Such polymers, which are known in the art as "metallocene", "single-site" or "constrained geometry" catalyzed polymers, are described in U.S. Pat. No. 5,472,775 to Obijeski et al. and assigned to the Dow Chemical Company, the entire contents of which are incorporated herein by reference. The metallocene process generally uses a metallocene catalyst which is activated, i.e. ionized, by a co-catalyst. Examples of metallocene catalysts include bis (n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, and zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow. However, numerous other metallocene, single-site and/or similar catalyst systems are known in the art; see for example, U.S. Pat. No. 5,539,124 to Etherton et al.; U.S. Pat. No. 5,554,775 to Krishnamurti et al.; U.S. Pat. No. 5,451, 450 to Erderly et al. and *The Encyclopedia of Chemical Technology*, Kirk-Othemer, Fourth Edition, vol. 17, Olefinic Polymers, pp. 765–767 (John Wiley & Sons 1996); the entire content of the aforesaid patents being incorporated herein by reference.

The core layer 12 also includes at least one filler. To ultimately create a breathable core layer 12, one or more types of fillers should desirably be added to the core layer polymer extrusion blend. These fillers can also be used to reduce the amount of polymer being used for the core layer 12, in addition to eventually imparting breathability. Both organic and inorganic fillers are contemplated for use with the present invention, provided they do not interfere with the film forming process and/or subsequent laminating processes. Examples of fillers include calcium carbonate ($CaCO_3$), various clays, silica ($SiO_2$), alumina, barium sulfate, sodium carbonate, talc, magnesium sulfate, titanium dioxide, zeolites, aluminum sulfate, cellulose-type powders, diatomaceous earth, gypsum, magnesium sulfate, magnesium carbonate, barium carbonate, kaolin, mica, carbon, calcium oxide, magnesium oxide, aluminum hydroxide, pulp powder, wood powder, cellulose derivatives, polymeric particles, chitin and chitin derivatives. The filler particles may optionally be coated with a fatty acid, such as stearic acid or behenic acid, and/or other material in order to facilitate the free flow of the particles (in bulk) and their ease of dispersion into the polymer. A particularly useful filler is calcium carbonate sold under the brand Supercoat®, of ECC International of Atlanta, Ga. The filled-film will desirably contain at least 35 percent filler based upon 35 the total weight of the film layer, more desirably from about 50 percent to about 65 percent by weight filler. Due to the nature of the polymer blend, roll blocking can occur when less than about 50 percent filler is utilized, roll blocking being the sticking which occurs between precursor film sheets when they are unwound from a roll. Thus, where lower levels of filler are used, additional processing aids and/or modification of the processing may be necessary to prevent such blocking.

In addition, the breathable filled core layer of the film may optionally include one or more stabilizers. Desirably the filled-film includes an anti-oxidant such as, for example, a hindered phenol stabilizer. Commercially available anti-oxidants include, but are not limited to, IRGANOX™ E 17 (a-tocopherol) and IRGANOX™ 1076 (octodecyl 3,5-di-tert-butyl4-hydroxyhydrocinnamate) which are available from Ciba Specialty Chemicals of Tarrytown, N.Y. In addition, other stabilizers or additives which are compatible with the film forming process, stretching and any subsequent lamination steps, may also be employed with the present invention. For example, additional additives may be added to impart desired characteristics to the film such as, for example, melt stabilizers, processing stabilizers, heat stabilizers, light stabilizers, heat aging stabilizers and other additives known to those skilled in the art. Generally, phosphite stabilizers (i.e. IRGAFOS 168 available from Ciba Specialty Chemicals of Tarrytown, N.Y. and DOVER-PHOS available from Dover Chemical Corp. of Dover, Ohio) are good melt stabilizers whereas hindered amine stabilizers (i.e. CHIMASSORB 944 and 119 available from Ciba Specialty Chemicals of Tarrytown, N.Y.) are good heat and light stabilizers. Packages of one or more of the above stabilizers are commercially available such as B900 available from Ciba Specialty Chemicals. Desirably about 100 to 2000 ppm of the stabilizers are added to the base polymer(s) prior to extrusion (Parts per million is in reference to the entire weight of the filled-film).

The low performance elastomer of the core layer may be present in amounts of between about 35 and 50 percent by weight of the core layer, with the filler desirably being present in amounts of between about 50 and 65 percent by weight of the core layer.

Alternatively, higher performance elastomeric styrenic-based block copolymer materials may be blended with the less elastic core material for the purpose of improving overall elastic performance (i.e. enhancing stretch and recovery properties). Such material is offered for sale under the Kraton® brand through the Shell Chemical Company. A suitable Kraton® elastomer includes Kraton® G1657. If a styrenic based block copolymer material is blended with the low performance elastomer, it is desirably present in an amount of between about 5 and 20 percent by weight of the core layer.

The multilayered product film 10c may include one or two skin layers, depending on the final use of the film. For instance, a two layered film may be more advantageous to avoid film blocking. A three layered film may be more advantageous for applications requiring a flat surface without surface buckling. The skin layers are desirably comprised of a second elastomer, a high performance elastomer and/or elastomer blends. Desirably, the skin layers are comprised of thermoplastic polyurethanes (TPU) or polyetheramides. Suitable thermoplastic polyurethanes are available from the Dow Chemical Company under the designation Pellethane® 2103-70A, or from the BF Goodrich Company under the designation Estane® 58245. Suitable polyetheramides are available from the Elf Atochem Company under the designations Pebax ® 2533 and 4033. Alternatively, the skin layers may include blends of these higher performance elastomers or additional higher performance elastomers which act as compatibilizers between the core and the skin layers. Such additional high performance elastomers include styrenic based block copolymers such as those available from the Shell Company under the brand Kraton® as previously described. Additionally, certain fillers may also be included in the skin layer to act as anti-blocking agents. Such fillers include those previously described. A particularly suitable skin layer antiblocking agent includes diatomaceous earth, such as that available from the Celite Corporation under the designation Super-floss. If present in the skin layer, such fillers are desirably present in an amount of between about 1 and 15 percent by weight of the skin layers, but more desirably around 10 percent.

In an alternate embodiment of the present invention, the skin layer may also include a compatibilizer for film coextrusion of dissimilar skin and core materials. The use of multilayer coextruded polyolefins and other nonpolar materials is common in the area of packaging and other film applications. However to coextrude materials that are incompatible, such as polar and nonpolar materials, a tie layer material is typically necessary. Without the use of a tie layer, the two dissimilar materials will not adhere well and the film will come apart. In accordance with this invention it has been found that when ethylene methyl acrylate (EMA) copolymer resin with a high methyl acrylate level is added to the skin layers of a multi- layer film, the bond between the skin and core layers is improved. Desirably, the methyl acrylate level is over about 20 percent. EMA acts as a compatibilizer to assist in the adhesion of the two incompatible materials. Essentially, nonpolar and polar materials can then be coextruded as a multilayer film with the addition of EMA into one of the layers. This provides the advantages of producing a single film which has the properties of more than one material.

In this regard, two or more layers of at least two incompatible materials can be extruded together into a multilayer film having the layer structure ABA, (A layers exemplified by reference 28 in FIG. 1) ABC, AB and any other permutation in which A represents one material, B represents a second material incompatible with A, and C represents yet another dissimilar and incompatible material. It is desirable for the EMA resin to be precompounded or dry blended prior to film extrusion into at least one of the materials. It is also desirable for the EMA level to be sufficiently high to promote the necessary adhesion, but not too high to jeopardize the properties sought from the primary skin material. It is therefore desirable for the EMA to be present in an amount between about 15–50 percent based on weight in the skin layers. Suitable EMA is available from the Exxon Chemical Company under the designation Exxon Optema® TC221 EMA. Exxon Optema EMA has a high percentage of methyl acrylate and so is softer and stickier, but more elastic. It is also somewhat breathable and adheres well to nonpolar support layers. In comparison, while EVA, which has been used in skin layers, will bond to nonpolar materials, it degrades at a lower temperature than EMA. Therefore, it will degrade on the lip of an extrusion die at times and need to be scraped off, resulting in reduction in operating efficiency.

The addition of EMA into at least one of the skin layers therefore provides the advantages of producing a single film which takes advantage of the properties of more than one material without the need for additional adhesive layers or the inclusion of adhesive materials in the thicker core layer. The more expensive and high performance elastomer can be used in less quantities in the thinner skin layers and a less expensive, low performance elastomer can be used in greater quantities in the thicker core layer.

Desirably, the total thickness of the product film 10c in FIG. 1 is between 0.6 and 1.2 millimeters and more desirably about 1.0 millimeter. The skin layers desirably have a total thickness of no more than 3 percent of the total film thickness or between approximately 0.018–0.04 millimeters (each film skin layer being approximately 0.009–0.02 millimeters), with the core layer of the product film thickness comprising approximately 97 percent of the total film thickness. It has been found that the product film demonstrates particularly improved combined elastomeric and breathability properties at approximately 50 percent ultimate stretch/elongation, as further defined below. The skin layers help to avoid die lip buildup as well.

The breathable product film 10c desirably comprises a filled barrier film having a WVTR of at least 1,000 $g/m^2/24$ hours, desirably in excess of 1,200 $g/m^2$ 124 hours, 1,500 $g/m^2/24$ hours or even 2,000 $g/m^2/24$ hours. In addition, the breathable stretched filled-product film desirably has a basis weight less than about 60 $g/m^2$ and even more desirably between about 15 and 40 $g/m^2$. The unstretched precursor film desirably has a basis weight of approximately 100 $g/m^2$ or less, and an overall thickness of about 3 millimeters.

Such multilayer films 10c can be formed by a wide variety of processes well known to those of ordinary skill in the film forming industry. Two particularly advantageous processes are cast film coextrusion processes and blown film coextrusion processes. In such processes, the two or three layers are formed simultaneously and exit the extruder in a multilayer form. Due to the extremely thin nature of the multilayer films according to the present invention, such processes will most likely prove to be the most advantageous, though it also may be possible to form multilayer films using separate extrusion processes. For more information regarding such processes, see, for example, U.S. Pat. No. 4,522,203 to Mays and U.S. Pat. No. 4,734,324 to Hill, which are incorporated herein by reference in their entirety.

Figure 3:
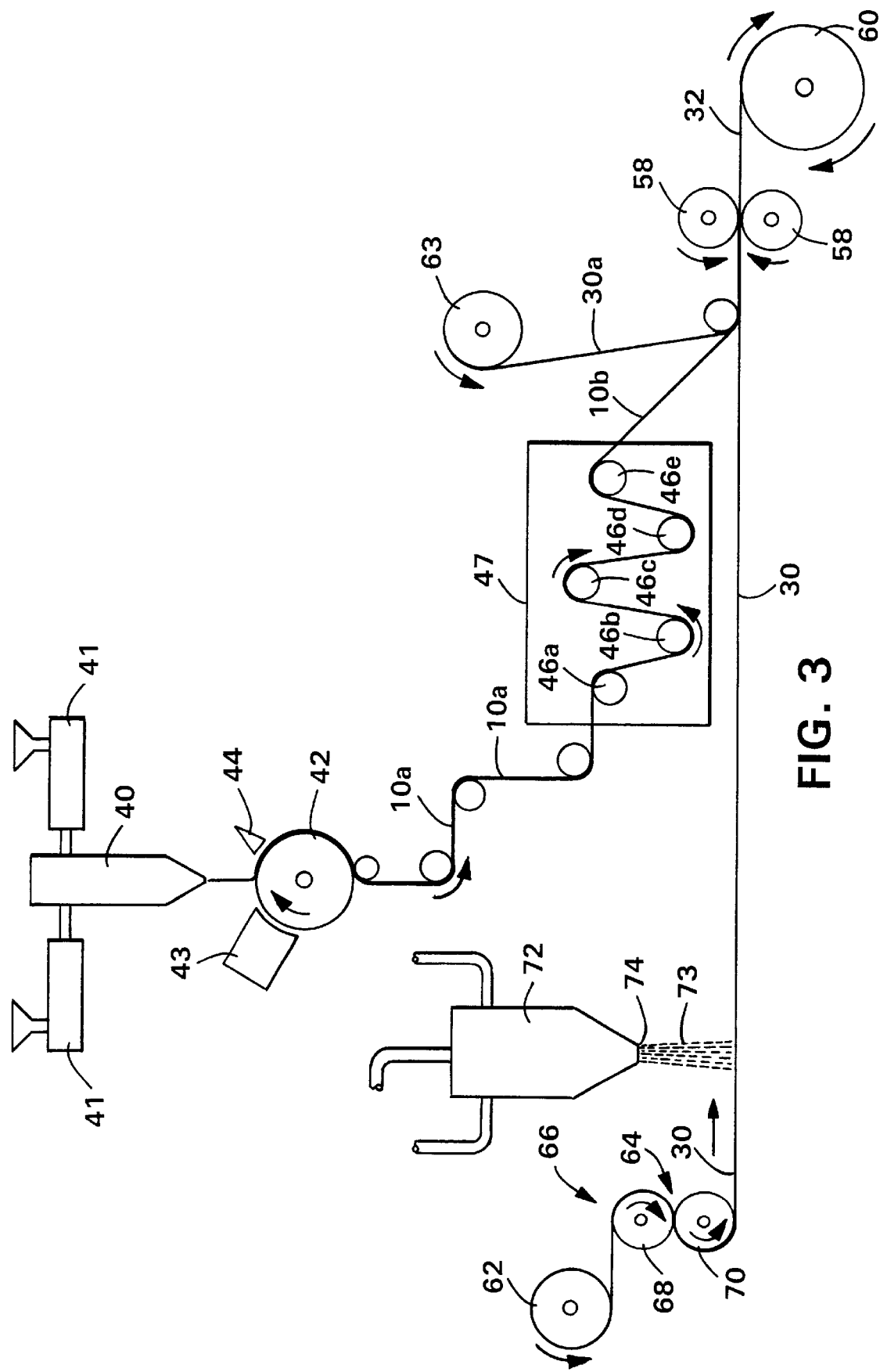
FIG. 3 is a schematic side view of a process for forming a multilayer film and a multilayer film/nonwoven laminate according to the present invention.

A process for forming the multilayer product film 10c is shown in FIG. 3 of the drawings. However, before a precursor film 10a is manufactured, the raw materials, i.e. the polymer(s) and filler must first be compounded through a process generally known to those skilled in the art. For instance, the raw materials can be dry mixed together and added into a hopper of a twin screw extruder. In the hopper, the materials are dispersively mixed in the melt and conveyed by the action of the intermeshing rotating screws. Upon exiting the twin screw extruder the material is immediately chilled and cut into pellet form.

Referring again to the figure, the multilayer precursor film 10a is formed from a coextrusion film apparatus 40 such as a cast or blown unit as was previously described above. Typically the apparatus 40 will include two or more polymer extruders 41. The compounded material is first directed into the film extruder (hoppers). Typically, material for the skin layer(s) is added to a smaller extruder while material for the core layer is added to a larger main extruder. As is generally known to those skilled in the art, but is described herein for ease of reference, the extruder is equipped with a flow plate that joins and directs the flow of the two extruders into the cavity of a film die (the lower portion of 40). A flow plate is used so that the flow of the smaller (skin layer) extruder is split and directed around the flow of the main extruder, so that it sandwiches the flow of the main extruder. In this way a multiple (three) layered flow exits the slot of the extruder die.

The multilayer film 10a is extruded onto a chill roll 42, which may be patterned. The flow out of the die 40 is immediately cooled on the chill roll 42. A vacuum box 43 situated adjacent the chill roll creates a vacuum along the surface of the roll to help maintain the precursor film 10a lying close to the surface of the roll. Additionally, air knives or electrostatic pinners 44 assist in forcing the precursor film 10a to the chill roll surface as it moves around the spinning roll. An air knife is a device known in the art which focuses a stream of air at a very high flow rate to the edges of the extruded polymer material. The result is the creation of a thin film with multiple layers. This thin precursor film 10a may be collected or subjected to further processing.

The three layer precursor film 10a construction, as initially formed, will have an overall thickness of approximately 2–3 millimeters and a basis weight of approximately 100 g/m$^2$ or greater, with the skin layers each having an initial thickness of 0.03–0.13 millimeters or greater, which collectively is approximately 3–5 percent of the overall initial precursor film thickness.

The precursor film 10a is subjected to further processing to make it breathable. Therefore, from the coextrusion film apparatus 40, the precursor film 10a is directed to a film stretching unit 47, such as a machine direction orienter or "MDO" which is a commercially available device from vendors such as the Marshall and Williams Company of Providence, Rhode Island. This apparatus 47 has a plurality of stretching rollers 46a–e which progressively stretch and thin the multilayer film in the machine direction of the film, which is the direction of travel of the film through the process as shown in FIG. 3. While the MDO is illustrated with five rolls, it should be understood that the number of rolls may be higher or lower depending on the level of stretch that is desired and the degrees of stretching between each roll. The film can be stretched in either single or multiple discrete stretching operations. Desirably, the unstretched filled film (precursor film) will be stretched from about 3 to about 6 times its original length, imparting a set in the stretched film 10b of between 3 to about 5 times of the original film length after the film is allowed to relax.

Referring again to FIG. 3, heated rolls 46a and 46b may act as preheat rolls. These first few rolls heat the film slightly above room temperature (90° F). Slow roll 46c travels at a circumferential speed slower than the following fast roll 46d. The different speeds of the adjacent rolls act to stretch the filled precursor film 10a. The rate at which the stretch rolls rotate determines the amount of stretch in the film, and thus the level of breathability. One or both of the slow roll 46c and fast roll 46d can be heated. After stretching, the film 10b may be allowed to slightly retract and/or be further heated or annealed by one or more heated rolls, such as by heated anneal roll 46e. These rolls are typically heated to about 120° F. to anneal the film. After the film exits the MDO and is allowed to relax, it includes a set/elongation as compared to the original precursor film typically of between 3 and 5 times the original length of the film. This total final stretch allows for breathability and additional stretch in the product film in at least the cross-machine direction, of up to about 50 percent elongation.

After exiting the MDO film stretching unit 47, the then breathable product film desirably has a maximum thickness of approximately 0.6–1.2 millimeters and the skin layers desirably have a total maximum thickness of no more than about 0.018–0.04 millimeters, which in turn is collectively about 3 percent of the overall film. At this point the stretch thinned filled product film may be wound for storage or proceed for further processing. The product film is then itself capable of being stretched an additional length, such as up to about 50 percent in the CD and some additional stretch in the MD.

If desired, the produced multilayer product film 10c may be attached to one or more support layers 30, such as fibrous layers, to form a multilayer film/laminate 32. Suitable laminate materials include nonwoven fabrics, multi-layered nonwoven fabrics, scrims, woven fabrics and other like materials. In order to achieve a laminate with improved body conformance, the fibrous layer is desirably an extensible fabric and even more desirably an elastic fabric. For example, tensioning a nonwoven fabric in the MD causes the fabric to "neck" or narrow in the CD and give the necked fabric CD stretchability. Examples of additional suitable extensible and/or elastic fabrics include, but are not limited to, those described in U.S. Pat. No. 4,443,513 to Meitner et al.; U.S. Pat. No. 5,116,662 to Morman et al.; U.S. Pat. No. 4,789,699 to Kieffer et al.; U.S. Pat. No. 5,332,613 to Taylor et al.; U.S. Pat. No. 5,288,791 to Collier et al.; U.S. Pat. No. 4,663,220 to Wisneski et al.; and U.S. Pat. No. 5,540,976 to Shawver et al. The entire content of the aforesaid patents are incorporated herein by reference.

Nonwoven fabrics which are to be laminated to such multilayered films desirably have a basis weight between about 10 g/m$^2$ and about 70 g/m$^2$ and even more desirably between about 15 g/m$^2$ and about 34 g/m$^2$. As a particular example, a 17 g/m$^2$ (0.5 ounces per square yard) web of polypropylene spunbond fibers can be necked a desired amount and thereafter laminated to a breathable stretched filled-product film 10b. The product film 10b would therefore be nipped (in lamination rolls of a calender roll assembly) to a necked or CD stretchable spunbond nonwoven web.

The film and spunbond material typically enter the lamination rolls at the same rate as the film exits the MDO. The outer nonwoven layer can be laminated to the breathable filled- product film by one or more means known in the art. The nonwoven layer and filled-film can be bonded, e.g. point bonded, by imparting sufficient energy to the film and/or fibrous fabric to cause the materials to soften and/or flow such as, for example, by applying thermal, ultrasonic, microwave and/or compressive force or energy. Bonding agents or tackifiers may be added to the film to improve adhesion of the layers. In a further aspect of the invention, the filled-film and fibrous layer can be adhesively laminated to one another. In order to achieve improved drape, the adhesive is desirably pattern applied to one of the fabrics or applied only to the outer fibrous layer. By applying the adhesive to the outer fibrous layer, such as a nonwoven fabric, the adhesive will generally only overlie the film at fiber contact points and thus provide a laminate with improved drape and/or breathability. Examples of suitable adhesives include, but are not limited to, REXTAC™ 2730 from Huntsman Corporation of Salt Lake City, Utah; H2525A which is a styrene block copolymer adhesive available from Findley Adhesives, Inc. of Wauwatusa, Wis.; and 34–5610 which is a styrene block copolymer adhesive available from National Starch, Starch and Chemical Co. of Bridgewater, N.J. Commercially available amorphous polyalphaolefins (APAO) used in hot melt adhesives suitable for use with the present invention include, but are not limited to, REXTAC™ ethylene-propylene APAO E-4 and E-5 and butylene-propylene BM-4 and BH-5 from Huntsman Corporation of Salt Lake City, Utah, and VESTOPLAST™ 792 from Huls AG of Marl, Germany. Desirably, about 1 g/m² to about 10 g/m² of adhesive is applied to a fibrous support fabric prior to superposing the support layer and filled-film. Additional bonding aids or tackifiers can also be used.

Figure 2:
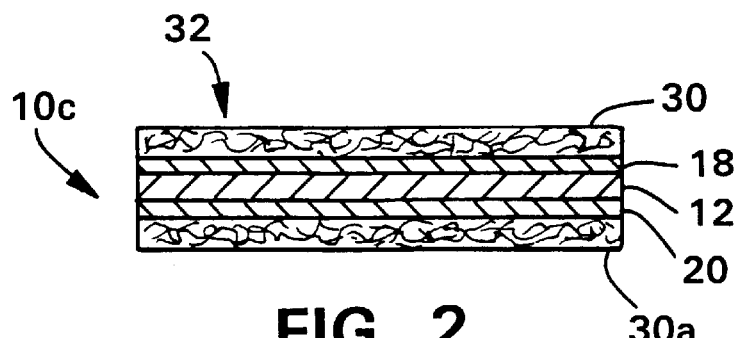
FIG. 2 is a cross-sectional side view of a multilayer film/nonwoven laminate according to the present invention.

Referring again to FIG. 3, a process is shown for creating a three layered laminate (as seen in FIG. 2) from a prefabricated extensible nonwoven material. A stretched filled product film 10b is shown being attached to an extensible fibrous layer 30, such as a necked spunbond web, to form a film/nonwoven laminate. A neckable material 30 is unwound from a supply roll 62. The neckable material 30 then travels in the direction indicated by the arrows associated therewith. The neckable material 30 then passes through the nip 64 of S-roll arrangement 66, formed by a stack of rollers 68 and 70, in a reverse S-wrap path, as indicated by the arrows associated with stack rollers 68 and 70. Because the circumferential or peripheral speed of the rollers of the S-roll arrangement 66 is controlled to be slower than the peripheral line speed of the downline calender roll assembly 58, as seen in FIG. 3, the neckable material 30 is tensioned so that it necks a desired amount. The necked material 30 could alternatively be necked off-line and unrolled in the tensioned, necked condition. The necked material 30 is maintained in the tensioned, necked condition as it passes under spray equipment 72 which sprays an adhesive 73 through adhesive die head 74 into the necked material 30. Once the stretched filled product film 10b has been sufficiently thinned, the necked material 30 formed and adhesive applied thereto, the layers can be brought together and the adhesive activated/treated (if necessary with heat) thereby forming the breathable laminate 32 as seen in FIG. 2.

Alternatively, a conventional fibrous nonwoven web forming apparatus, such as a pair of spunbond machines (not shown), may be used to form the support layer 30 in an in-line process. In such an in-line process, the long, essentially continuous fibers would be deposited onto a forming wire as an unbonded web. The unbonded web would then be sent through a pair of bonding rolls to bond the fibers together and increase the tear strength of the resultant web support layer. One or both of the rolls may be heated to aid in bonding. Typically, one of the rolls is also patterned so as to impart a discrete bond pattern with a prescribed bond surface area to the web. The other roll is usually a smooth anvil roll but this roll also may be patterned if so desired. Once the multilayer product film has been sufficiently thinned and oriented and the support layer has been formed, the two layers would then be brought together and laminated to one another using a pair of laminating rolls or other means.

As with bond rolls, the laminating rolls 58 may be heated. Also, at least one of the rolls may be patterned to create a discrete bond pattern with a prescribed bond surface area for the resultant laminate. Desirably, the maximum bond point surface area for a given area of surface on one side of the laminate will not exceed about 50 percent of the total surface area. There are a number of discrete bond patterns which may be used such as the H&P bond pattern, the C-star bond pattern or the Baby Object bond pattern. See, for example, Brock et al., U.S. Pat. No. 4,041,203, which is incorporated herein by reference in its entirety. Once the laminate exits the laminating rolls, it would be wound up into a roll for subsequent processing. Alternatively, the laminate may continue in-line for further processing or conversion.

The process shown in FIG. 3 also may be used to create a three layer laminate 32 such as is shown in FIG. 2 of the drawings. The only modification to the previously described process is to feed a supply 63 of a second fibrous nonwoven web support layer 30a into the laminating rolls 58 on a side of the multilayer product film 10b opposite that of the other fibrous nonwoven web support layer 30. As shown in FIG. 3, the supply of support layer 30 is in the form of a pre-formed roll 62. Alternatively, as with the other layers, the support layer 30 may be formed directly in-line. In either event, the second support layer 30a is fed into the laminating rolls 58 and is laminated to the multilayer product film 10c in the same fashion as the first support layer 30.

As has already been stated, once the laminate 32 is produced, the material continues on to the winder 60. As the material moves to the winder 60, it is allowed to retract. This is achieved by slowing the speed of the winder 60 to adjust for the retraction of the material. This process allows for machine direction stretch in the material since the spunbond has "bunched up" along with the retracting film and therefore has "give" when stretched in the machine direction in the finished laminate 32.

Figure 4:
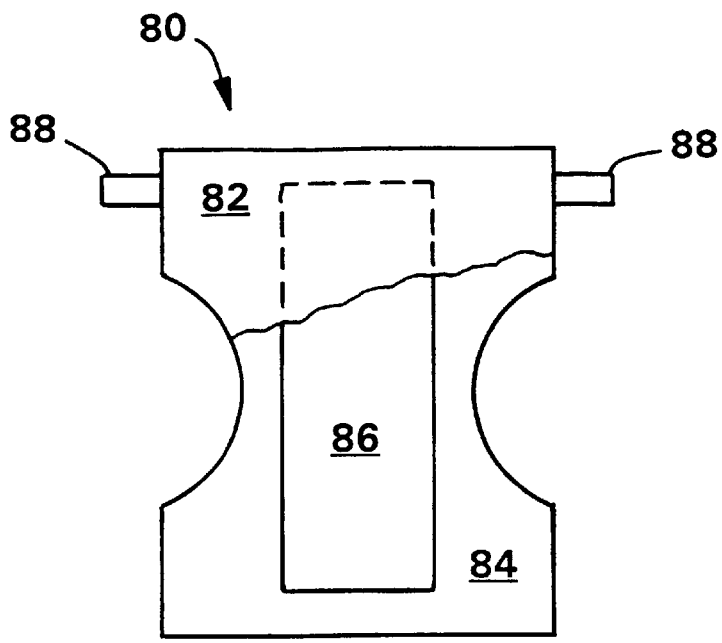
FIG. 4 is a partially cut away top plan view of an exemplary personal care absorbent article, in this case a diaper, which utilizes a multilayer film and multilayer film/nonwoven laminate according to the present invention.

As has been stated previously, the multilayer product film 10b and the multilayered product film 10c in a laminate 32 may be used in a wide variety of applications, not the least of which includes personal care absorbent articles such as diapers, training pants, incontinence devices and feminine hygiene products such as sanitary napkins. An exemplary article 80, in this case a diaper, is shown in FIG. 4 of the drawings. Referring to FIG. 4, most such personal care absorbent articles 80 include a liquid permeable top sheet or liner 82, a back sheet or outercover 84 and an absorbent core 86 disposed between and contained by the top sheet 82 and back sheet 84. Articles 80 such as diapers may also include some type of fastening means 88 such as adhesive fastening tapes or mechanical hook and loop type fasteners.

The multilayer product film 10c by itself, or in other forms, such as the multilayer film/support layer laminate 32 may be used to form various portions of the article including, but not limited to, the top sheet 82 and the back sheet 84. If the film is to be used as the liner 82, it will most likely have to be apertured or otherwise made to be liquid permeable. When using a multilayer film/nonwoven laminate 32 as the outercover 84, it is usually advantageous to place the nonwoven side facing out away from the user. In addition, in such embodiments it may be possible to utilize the nonwoven portion of the laminate 32 as the loop portion of the hook and loop combination.

Other uses for the multilayer film and multilayer film/nonwoven laminates according to the present invention include, but are not limited to, surgical drapes and gowns, wipers, barrier materials and garments/articles of clothing or portions thereof including such items as workwear and lab coats.

In this fashion, a higher cost, higher performance elastomer material may be efficiently used in less amounts in the skin layers of a multilayered film laminate to buttress the performance of a low performance elastomer, which makes up the majority of the film in the film core layer. By using the higher performance elastomer in the skin layer(s), the film retains a relatively high level of breathability and yet still demonstrates elastic behavior, particularly at approximately 50 percent stretch in the cross-machine direction. In particular, the high performance elastic skin layers will improve the retraction and reduce the percent set of the product film, that is the percentage of elongation at which the retraction tension goes to approximately zero.

The present invention is further described by the trial examples which follow. Such trial examples, however, are not to be construed as limiting in any way either the spirit or the scope of the present invention.

TESTS

Melt Index: The melt index (MI) is a measure of the viscosity of a polymer at a given set of conditions. The MI is expressed as the mass of material which flows from a capillary of known dimensions under a specified load or shear rate for a measured period of time and is measured in grams/10 minutes at 190° C. and load of 2160 g according to ASTM test 1238-90b.

WVRR: The water vapor transmission rate (WVTR) for the sample materials was calculated in accordance with the following test method. Circular samples measuring three inches in diameter were cut from each of the test materials and a control which was a piece of CELGARD® 2500 film from Hoechst Celanese Corporation of Sommerville, N.J. CELGARD® 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at about 100° F. (38° C.) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed and immediately returned to the oven. After 24 hours, the pans were removed from the oven and weighed again. The preliminary test water vapor transmission rate values were calculated with Equation (I) below:

(I) Test WVTR=(grams weight loss over 24 hours)×315.5 g/m$^2$/24 hours

The relative humidity within the oven was not specifically controlled.

Under the predetermined set conditions of about 100° F. (38° C.) and ambient relative humidity, the WVTR for the CELGARD® 2500 control has been defined to be 5000 grams per square meter for 24 hours. Accordingly, the control sample was run with each test and the preliminary test values were corrected to set conditions using Equation (II) below:

(II) WVTR=(Test WVTR/control WVTR)×(5000 g/m$^2$/24 hours)

Peel test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape or some other suitable material in order to prevent the film from ripping apart during the test.

The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position and the clamps move apart at the specified rate of extension to pull the laminate apart. The sample specimen is pulled apart at 180° of separation between the two layers and the peel strength reported as an average of peak load in grams. Measurement of the force is begun when 16 mm of the laminate has been pulled apart and continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Ma. 02021, or the Thwing-Albert Model INTELLECT II available from the Thwing-Albert Instrument Co., 10960 Dutton Rd., Phila., Pa. 19154, may be used for this test. Results are reported as an average of three specimens and may be performed with the specimen in the cross direction (CD) or the machine direction (MD).

Extension/Retraction: Sintech tests included a two-cycle, 50 percent ultimate (target) elongation extension test (that is a predefined point of elongation) with the first cycle extension tension and second cycle retraction tension taken at 30 percent, and a two cycle, 100 percent extension test with a first cycle extension tension and second cycle retraction tension taken at 50 percent. For the 50 percent ultimate elongation extension test, the sample is first elongated to an ultimate elongation of 50 percent and then allowed to retract/recover to an amount where the amount of resistance is zero. Testing is done on the Sintech 1/S or 2/S equipment utilizing TESTWORKS for Windows 3.02 software to record data. In conducting an extension /retraction test, a 3 inch wide sample of the material is held within clamps (3 inch gauge length for 100 percent and 4 inch gauge length for 50 percent) and pulled to a target elongation of either 50, or 100 percent at a rate of 500 mm/min, and returned to the original distance, typically of four inches, for two cycles. The test was done at ambient temperature and humidity conditions.

Hysteresis is calculated in accordance with the following equation:

$$\mathrm{Hysteresis} = \frac{\text{Force of Extension (1}^{\text{st}}\text{ cycle)} - \text{Force of Retraction (2}^{\text{nd}}\text{ cycle)}}{\text{Force of Extension (1}^{\text{st}}\text{ cycle)}} \times 100$$

Hydrohead. A measure of the liquid barrier properties of a fabric is the hydrohead test. The hydrohead test determines the height of water or amount of water pressure (in millibars) that the fabric will support before liquid passes therethrough. A fabric with a higher hydrohead reading indicates it has a greater barrier to liquid penetration than a fabric with a lower hydrohead. The hydrohead can be performed according to Federal Test Standard 191A, Method 5514. The hydrohead data cited herein was obtained using a test method similar to the aforesaid Federal Test Standard except as modified and noted below. The hydrohead was determined using a hydrostatic head tester available from Mario Enterprises, Inc. of Concord, N.C. The specimen is subjected to a standardized water pressure (as opposed to a column of water as in the Federal Test Standard) which is increased at a constant rate until leakage appears on the surface of the fabric in three separate areas. (Leakage at the edge, adjacent to the clamps is ignored.) Unsupported fabrics, such as thin film, can be supported to prevent premature rupture of the specimen.

Trial Example Conditions

Elf Atochem Pebax®4033 and 2533, Dow Pellethane® 2103-70A, and BF Goodrich Estane®58245 were dried for three hours at 1500 F prior to compounding. Exxon Optema® TC EMA was blended with many of the trial compounds to act as a compatibilizer and adhesion promoter when coextruding mostly polar skin layer materials with non-polar filled polyethylene core layers. The filler was coated for each sample with stearic acid at 1% by weight prior to compounding. A two extruder system was utilized to coextrude the skin layers and core layer in an ABA type structure with "A" representing the skin layers and "B" representing the core layer.

Trial Operating Conditions

The target melt temperature for the core layers was 420° F. while the target melt temperature of the skin layers was 380°F. It should be noted that the melt temperature varied with each compound's melt flow. For the purposes of these trials, the MDO included six stretch rolls. These included two preheat rolls, two fast rolls identified as F1 and F2 and two annealing rolls, the second of which is identified as A2. Lamination rolls follow the six rolls and are identified as "Lam".

The trial example core layers were comprised of two formulations. The first formulation, identified as P5492-106A (106A), included 20% Dow Engage EG8200, 20% Dow Affinity PL1845, 60% ECC Supercoat calcium carbonate and 600 ppm Irganox E17. The second formulation, identified as P5492-106E (106E), included 17.5% Dow Engage EG8200, 17.5 % Dow Affinity PL 1845, 10% Kraton G1657, 5 % ECC Supercoat calcium carbonate and 600ppm Irganox E17.

While the first core layer was run with many possible skin formulations, the second core layer formulation was run only with EMA/Kraton® and Pebax®/Kraton® blends. Three stretching and lamination trials were run using 45% necked polypropylene nonwoven spunbond obtained from the Kimberly-Clark Corporation. In certain trials the spunbond used consisted of flexible polyolefin spunbond and such is identified by "FPO". The term flexible polyolefin refers to polyolefin materials containing propylene based polymer with controlled regions of atactic polypropylene units to achieve a desired crystallinity such as described in U.S. Pat. No. 5,910,136 entitled "Oriented Polymeric Microporous Films with Flexible Polyolefins and Methods of Making the Same" to Hetzler and Jacobs; the entire contents of which are incorporated herein by reference in its entirety.

Stretchable bicomponent spunbond (FPO/PP) has both MD and CD stretch properties. This material has demonstrated stretch extensions between 50 and 75%, soft hand, fiber crimping at ambient FDU (fiber draw unit) temperature, and the strength of traditional spunbond. Sheet materials have been produced containing polypropylene side by side (S/S) with flexible polyolefins. FPO polymers for use in S/S bicomponent PP spunbond may be obtained from the Rexene Corp. of Texas. Similarly, sheet materials can be produced with a sheath/core fiber arrangement (S/C). Fiber sizes of 14 microns and higher have been used in the material. Polymer ratios can range from 50/50 to 70/30 PP/FPO. The FPO/PP spunbond can be utilized as a stretchable member of a disposable personal care product, such as a diaper liner, diaper outer cover, hook and loop fastener base, a substitute for necked spunbond material, a component of film laminates, and a component of other laminates where stretch and recovery are desired. Stretchable bicomponent spunbond (FPO/PP) can be made in-line in one step. Fabric produced from such process exhibits recovery from stretch due to inherent elasticity. Further description of flexible polyolefins can be found in U.S. Pat. No. 5,723,546 to Sustic and assigned to the Rexene Corporation. In particular, such nonwoven sheets include Huntsman deformable polyolefin/polypropylene bicomponent spunbond fiber (FPO/PP) sold under the brand REXFLEX FLEXIBLE POLYOLEFINS. Bicomponent spunbond is approximately 70% polypropylene and 30% flexible polyolefins.

In order to isolate the effects of the various skin layers, monolayer films using both core compound formulations were also stretched and laminated as controls during each of the respective trials. A variety of skin layer formulations were run and evaluated as listed in the following Table 1.

TABLE 1

Skin Layer Formulations

1.) 30% Exxon Optema ® TC221 EMA
60% Elf Atochem Pebax ® 2533
Polyetheramide
10% Diatomaceous Earth
2.) 30% Exxon Optema ® TC221 EMA
60% Elf Atochem Pebax ® 4033
10% Diatomaceous Earth
3.) 30% Exxon Optema ® TC221 EMA
60% Dow Pellethane ® 2103-70A TPU
10% Diatomaceous Earth
4.) 45% Exxon Optema ® TC221 EMA
45% Shell Kraton ® G1657
10% Diatomaceous Earth
5.) 30% Shell Kraton ® G1657
60% Elf Atochem Pebax ® 4033
Polyetheramide
10% Diatomaceous Earth Trial Example 1

Conditions: The following conditions were set for the first stretching and lamination trials.

| | |
|---|---|
| MDO Rolls 1–6 Temperatures | 90° F., 90° F., Ambient, 110° F., 110° F., Ambient |
| Adhesive | Rextac 2730 @ 2 grams per square meter (gsm) add on |
| Unwind Speed | 63 feet per minute (fpm) |
| Winder Speed | Varied |
| F2/F1 (speed ratio) | 3.5X |
| Lam/A2 (speed ratio) | 0.92–0.880 |
| Hot Melt Die Melt Temp. | 345° F. |
| Hot Melt Die Air Temp. | 365° F. |
| Forming Height | 3 inch |
| Bonder Pattern Surface | 250° F.(Baby Objects) |

The facing used in this trial was a 20 inch wide 45% necked polypropylene spunbond obtained from the Kimberly-Clark Corporation. A rubber anvil and Baby Objects pattern roll were used for thermal lamination steps. All film samples were adhesively laminated, but only six films could be thermally laminated. All film samples were successfully adhesively laminated to the 45% necked polypropylene spunbond. It should be noted that the Pellethane/EMA sample had a hard edge due to poor film gauge uniformity of the roll, which promoted blocking in the wound film roll. The pattern roll temperature was raised from 200° F. to 250° F., to improve thermal lamination adhesion, but that still did not appear to be enough for any thermal laminates. The films were stretched until complete whitening occurred. This was done between the F1/F2 rolls at 3.0× to 3.5×. While the majority of retraction occurred prior to the laminator, the winder speed was decreased slightly to allow for residual retraction of the films. The resulting final stretch on the laminates was approximately 2.5–2.7× the original length. Those films containing Kraton® in the core needed to be stretched 4.0× for complete whitening to occur.

Trial Example 2

Conditions: The following conditions were set for the second stretching and lamination trials.

| | |
|---|---|
| MDO Rolls 1–6 Temperatures | 90° F., 90° F., Ambient, 110° F., 110° F., Ambient |
| Adhesive | Rextac 2730 @ 3 gsm add on |
| Unwind Speed | 57 fpm |
| Winder Speed | Varied with retraction |
| F2/F1 (speed ratio) | 5.0X–5.5X |
| Lam/A2 (speed ratio) | 0.95–1.0 (decreased with increased elasticity) |
| Hot Melt Die Melt Temp. | 345° F. |
| Hot Melt Die Air Temp. | 365° F. |
| Forming Height | 3 inch |

The following skin formulations and core formulations were tested in trial 2.
1.) EMA/Pebax® 4033 blend on the first core formulation
2.) EMA/Pebax® 2533 blend on the first core formulation
3.) EMA/Pellethane® blend on the first core formulation
4.) Kraton/Pebax® 4033 blend on the second core formulation
5.) EMA/Kraton® blend on the second core formulation
6.) First core formulation layer as the control
7.) Second core formulation layer as the control The facing used in this trial was a 45 percent necked polypropylene spunbond obtained from the Kimberly-Clark Corporation. These films were re-run to achieve MD stretch as well as CD stretch with non-MD extensible spunbond. The tensioned films were adhesively laminated to the spunbond while elongated and the laminate was allowed to retract prior to being wound on the winder. This allowed for MD extensibility in the film/spunbond laminate. The retraction varied from 12–26 percent MD, as shown in the following Table 2, based on winder-to-laminator speed ratios. The resultant total stretch on the films was therefore between 4.0–4.9x. The adhesive add-on was increased from 2–3 gsm to address problems in obtaining proper adhesion of the film to the spunbond. These films had been stored under pressure of other rolls on top of them and therefore tended to suffer from film blocking more than earlier run samples. Therefore only five films could be successfully laminated. The running conditions varied somewhat depending on the type of film and how badly it was blocked. The extensibility of these materials were measured in the MD direction. It should be noted that larger values for MD extensibility are preferred. The data is reflected in the following Table 2.

MD EXTENSIBILITY
BASED ON MACHINE RETRACTION

| SAMPLE | % MD EXTENSIBILITY |
|---|---|
| 106A CONTROL | 12% |
| 30% EMA TC221<br>60% Pebax ® 2533<br>10% Antiblock | 16%** |
| 30% EMA TC221<br>60% Pellethane<br>10% Antiblock | 19%** |
| 106E CONTROL | 13.5% |
| 30% Kraton ® G1657<br>60% Pebax ® 4033<br>10% Antiblock *w/106E | 26% |

**These films delaminated and could not be cycle tested properly.

Trial Example 3

Conditions: The following conditions were set for the third stretching and lamination trials. Flexible Polyolefin (FPO) spunbond was utilized, obtained from the Kimberly-Clark Corporation, with the FPO obtained from the Rexene Corporation.

| | |
|---|---|
| MDO Rolls 1–6 Temperatures | 90° F., 90° F., Ambient, 110° F., 110° F., Ambient |
| Adhesive | Findley 2525A @ 3 gsm add on |
| Unwind Speed | 42 fpm |
| Winder Speed | Varied with retraction |
| F2/F1 (speed ratio) | 4.75X–5.0X |
| Lam/A2 (speed ratio) | 0.95–1.0 (decreased with increased elasticity) |
| Hot Melt Die Melt Temp. | 345° F. |
| Hot Melt Die Air Temp. | 365° F. |
| Forming Height | 3 inch |

The following skin formulations and core formulations were tested in trial example 3.

1.) EMA/Pebax® 2533 blend on a first core formulation
2.) EMA/Pellethane® blend on a first core formulation
3.) Kraton® G1657/Pebax® 4033 blend on a second core formulation There appeared to be good adhesion to the flexible polyolefin spunbond after adhesive lamination with the Findley adhesive. The films did not visually contain any holes. The films with Kraton® blended cores (106E) demonstrated better elastic performance. The Findley adhesive was fairly tacky and often bled through the spunbond, causing the laminate to block somewhat. It was observed that this adhesive stayed molten longer than the Rextac and occasionally the molten strands would agglomerate and burn small holes in the film. These films were allowed to retract fully prior to the winder but after the laminator, so that MD extensibility could be achieved. A few of the films required some slight retraction prior to adhesive lamination in order to reduce the film tension as it came off of the MDO. The reduced tension helped avoid film breaks. The films demonstrated MD retraction of 16.5 –19 percent.

SUMMARY OF TRIAL EXAMPLE TESTING

A) Lamination Trial Example 3 Test Results at 3–3.5x Stretch

The base breathability of the films was demonstrated by the 106A core control sample at approximately 3,000 g1m$^2$ 24 hours. Samples with Kraton® in the skin layer inhibited breathability somewhat. All films with a core layer of 106E formulation had significantly lower breathability results. Films containing skin with high performance elastomers such as Pebax® 2533, 4033, Pellethane® and Kraton® demonstrated breathability 55 to 89 percent of the control core layer film. The following table 3 reflects these results.

Table 3 illustrates the WVTR test results for the various test samples.

TABLE 3

WVTR Test Results

Water Vapor Transmission Rate, g/m²/day

| Core Layer (composition) | Skin Layer (composition) | 3.5X Stretch First Trial | | 4.75X Stretch Third Trial | 5.5X Stretch Second Trial | |
|---|---|---|---|---|---|---|
| 106A (60% filler, mPE) | none | 3000 | 100% | — | 4450 | 100% |
| 106A (60% filler, mPE) | (EMA/Peb 2533) | 1726 | 57.5% | 2289 | 2850 | 64% |
| 106A (60% filler, mPE) | (EMA/Pellethane) | 2092 | 69.7% | 3132 | 3640* | 81.8% |
| 106A (60% filler, mPE) | (Kraton/Peb 4033) | 1643 | 54.8% | — | 2480 | 55.7% |
| 106A (60% filler, mPE) | (Kraton/EMA) | 2383 | 79.4% | | | |
| 106A (60% filler, mPE) | (EMA/Peb 4033) | 2685 | 89.5% | | | |
| 106A (60% filler, mPE) | (EMA/a.b.) | 3179 | 106.0% | | | |
| 106E (55% filler, 35% mPE, 10% Kraton) | none | 1400 | 100% | | 4270 | 100% |
| 106E (55% filler, 35% mPE, 10% Kraton) | (Kraton/Peb 4033) | 1188 | 84.9% | 1629/ 1325 | 2480 | 58.1% |
| 106E (55% filler, 35% mPE, 10% Kraton) | Kraton/EMA | 1485 | 106.1% | | | |

*Only 5X stretch

B) Lamination Trial Example 2 Test Results

The breathability of the laminates increased for the second lamination trial. Originally, the film was extended 3.5× and allowed to retract before it was adhesively laminated. In the later trial it was stretched 5.5×, kept under the stretch tension, adhesively laminated and then the laminate was allowed to retract. Both MD and CD extensibility were obtained in the process. The resulting final stretch ratio of the film was much higher at between 4.08 to 4.86 during this trial. The film with the Pellethane® blended skin layer demonstrated higher WVTR values than the film with a similar formulation using Pebax® 2533. This was also the case in the first trial. The WVTR of the Pebax® 4033 blended skin layer film with the 106E core more than doubled from 1188 at the low stretch, to 2480 at the higher stretch ratio.

The skin layers appeared to hinder breathability for the films in both the first and second trial examples. However, the WVTR results were acceptable but lower than the control films. The films with the skin layers tended to retract more and result in lower final stretch than the control films. These results are reflected in the following Table 4.

TABLE 4

WVTR & STRETCH OF SECOND TRIAL LAMINATES
Selected Skin Multi-Layers Plus Control Layers
5.0X–5.5X Stretch

| SAMPLE | MDO Stretch | Final Stretch | WVTR |
|---|---|---|---|
| 1) 30% EMA TC221 60% Pebax ® 2533 10% Antiblock 106A core | 5.5X | 4.08X | 2850 |
| 2) 30% EMA TC221 60% Pellethane ® 10% Antiblock 106A core | 5.0X | 4.18X | 3640 |
| 106A core 60% CaCO3 40% Met PE | 5.5X | 4.86X | 4450 |
| 3) 30% Kraton ® 60% Pebax ® 4033 10% Antiblock 106E Core layer | 5.5X | 4.08X | 2480 |
| 4) 106E core 55% CaCO3 35% Met PE 10% Kraton ® | 5.5X | 4.75X | 4270 |

Hydroheads for all of the above were in excess of 150 mbar.

TABLE 5

MD AND CD CYCLE TEST FOR SECOND TRIAL LAMINATES
Skin Multi-Layers Plus Control Layers
5.5X Stretch

| SAMPLE | CD-50% Test 30% Ext 1 | CD-50% Test 30% Ret 2 | Hysteresis CD @ 30% | MD-20% Test 10% Ext 1 | MD-20% Test 15% Ext 1 | MD-20% Test 20% Ext 1 |
|---|---|---|---|---|---|---|
| 106A Layer 60% CaCO3 40% Met PE | 322 | 77 | 76.1 | 1198 | 1870 | 4298 |
| 106E Layer 55% CaCO3 35% Met PE 10% Kraton ® | 324 | 78 | 76 | | | |
| Skin Layer w/106E core 30% Kraton ® 60% Pebax ® 10% Antiblock | 389 | 103 | 73.5 | 914 | 1312 | 1669 |

Extension and Retraction Tension Results are in gram units. Hysteresis and Set Results are %.
These films could not be properly tested to the full 50% elongation Cycle in the MD.

SUMMARY

The Pebax blended skin layer films tended to demonstrate the higher retraction and therefore the lower WVTRs. This elasticity in the skin layers appears to be a factor in the resulting lower WVTRs.

The three layered films of Trial Example Three were run again at high stretch ratios (4.75–5.0) and allowed to retract after the adhesive and facing were applied to allow for MD and CD stretch in the laminates. With the Findley 2525A adhesive, none of the delamination problems were observed as in the previous trial. The flexible polyolefin spunbond was primarily used in this trial instead of the necked polypropylene spunbond.

The Kraton®/Pebax® skin layer film with the 106E core was run in three different variations. It was run with FPO spunbond with a slight retraction between the last MDO roll and before the adhesive laminator (0.95 ratio between the last MDO roll and laminator), without any retraction prior to the laminator (ratio of 1.0) with FPO spunbond, and again without any retraction prior to lamination while using the 45 percent necked spunbond. The slight retraction prior to laminating reduced the overall WVTR of the film. No significant difference was seen in WVTR for the film laminated to the necked spunbond over the FPO material. This data is reflected in the following Table 6.

TABLE 6

WVTR, PEELS & STRETCH OF THIRD TRIAL LAMINATES
Selected Skin Multi-Layers Plus Control Layers
4.75X–5.5X Stretch

| SAMPLE | MDO Stretch | Final Stretch | WVTR | Laminate Peels | Basis Wt |
|---|---|---|---|---|---|
| 1) 30% EMA TC221 60% Pebax ® 2533 10% Antiblock 106A Core/FPO SB | 4.75X | 3.87 | 2289 | 524 | 89.4 |
| 2) 30% EMA TC221 60% Pellethane ® 10% Antiblock 106A Core/FPO SB | 4.75X | 3.87 | 3132 | 310 | 90 |
| 3) 106A core 60% CaCO3 40% Met PE Necked SB | 5.5X | 4.86 | 4450 | poor <50 | |
| 4) 30% Kraton ® 60% Pebax ® 4033 10% Antiblock 106E core/FPO (1.0) | 4.75X | 3.87 | 1570 | N.M. | 110.8 |
| 5) 30% Kraton ® 60% Pebax ® 4033 10% Antiblock 106E core/FPO (.95) | 4.75X | 3.85 | 1325 | N.M. | 105.3 |
| 6) 30% Kraton ® 60% Pebax ® 4033 10% Antiblock 106E core/Necked SB (.95) | 4.75X | 3.85 | 1629 | 143 | 88.3 |

TABLE 6-continued

WVTR, PEELS & STRETCH OF THIRD TRIAL LAMINATES
Selected Skin Multi-Layers Plus Control Layers
4.75X–5.5X Stretch

| SAMPLE | MDO Stretch | Final Stretch | WVTR | Laminate Peels | Basis Wt |
|---|---|---|---|---|---|
| 7) 106E core<br>55% CaCO3<br>35% Met PE<br>10% Kraton ®<br>Necked SB | 5.5X | 4.75 | 4270 | poor<br><50 | |

Hydroheads for all above were in excess of 150 mbar.
*N.M. - not measured because peel could not be initiated.

Two cycle stretch tests at 50 percent and 100 percent elongation were run (as previously described) on five replicates of each sample after it had been laminated to a spunbond material. The 50 percent elongation tests in the CD direction gave comparable-to-better results for stretch and recovery tensions at 30 percent compared to the control. The results are illustrated in the following Table 7.

The samples did not perform as well for the 100 percent elongation. It is theorized that the 100 percent elongation was beyond the elastic range of the metallocene-catalyzed polyethylene core and the necked spunbond since high percent set results were observed at that level.

The relative effects of the skin layers on the core layers are illustrated in Table 5–6. The results showed better

TABLE 7

| Skin Formula | 30% Ext 1 50% cycle | 50% Ext 1 100% cycle | 30% Ret 2 50% cycle | 50% Ret 2 100% cycle | Hyst 1/2 @30%/@50% | Ext @Set 2 50%/100% |
|---|---|---|---|---|---|---|
| 100% Ampacet Skin | 637 | 762 | 154 | 40 | 75.8/94.8 | 14.74/42.74 |
| 30% EMA TC221<br>60% Pebax 4033<br>10% Antiblock | 597 | 706 | 146 | 38 | 75.6/94.6 | 14.85/43.45 |
| 30% EMA TC221<br>60% Pebax 2533<br>10% Antiblock | 568 | 671 | 149 | 46 | 73.8/93.1 | 14.29/41.34 |
| 30% EMA TC221<br>60% Pelethane<br>10% Antiblock | 505 | 630 | 139 | 52 | 72.5/91.7 | 14.76/40.30 |
| 80% EMA TC221<br>20% Antiblock | 508 | 643 | 130 | 32 | 74.5/95.0 | 15.4/43.62 |
| 80% FPO W300<br>20% Antiblock | 638 | 729 | 150 | 31 | 76.6/95.7 | 15.24/44.31 |
| 45% EMA TC221<br>45% Kraton G1657<br>10% Antiblock | 614 | 691 | 140 | 34 | 77.1/95.1 | 14.95/43.38 |
| 48% EMA TC221<br>48% FPO W300<br>4% Antiblock | 676 | 711 | 156 | 26 | 76.9/96.3 | 15.07/45.53 |
| 55% EVA LD 760<br>35% FPO W300<br>10% Antiblock | 569 | 665 | 138 | 36 | 75.8/94.6 | 15.03/43.29 |
| 30% Kraton G1657<br>60% Pebax 4033<br>10% Antiblock | 626 | 754 | 152 | 39 | 75.7/94.2 | 14.7/43.35 |
| 30% **Kraton G1657<br>60% Pebax 4033<br>10% Antiblock | 543 | 678 | 156 | 70 | 71.3/89.7 | 12.05/34.22 |
| 45% **EMA TC221<br>45% Kraton G1657<br>10% Antiblock | 534 | 658 | 156 | 79 | 70.8/88.0 | 11.76/32.79 |
| 45% ***EMA TC221<br>45% Kraton G1657<br>10% Antiblock | 559 | 652 | 163 | 78 | 70.7/88.0 | 11.52/33.04 |
| 60% CaCO3 (106A)<br>40% Affinity/Engage | 603 | 701 | 146 | 33 | 75.8/95.3 | 14.60/43.7 |
| 55% CaCO3 (106E)<br>35% Affinity/Engage<br>10% Kraton G1657 | 635 | 696 | 182 | 72 | 71.3/89.7 | 11.64/34.38 |

Extension Tension(Ext 1) and Retraction Tensions(Ret 2) are in gram units. Hysteresis(Hyst 1/2) & Set results are in %.
**with 106E Core layer
***106E Core layer and this film was retracted to a higher percent prior to being laminated in the lamination process.

hysteresis and set with the Kraton® blended control film (106E) and with the films coextruded with this core formulation. These films demonstrated especially higher retraction tensions (Ret2) relative to the corresponding extension tensions (Ext1) and therefore an improved hysteresis. The skin layers coextruded with the 106Acore formulation and containing Pebax® 2533 and Pellethane® demonstrated comparable high hysteresis values.

Conclusions of Trial Examples

The multilayered films with the Pebax® and the Pellethane® blended skins provided an improvement over control films without skin layers for elastic properties at 50 percent elongation. While these films did demonstrate lower WVTRs than the control film, they still exhibited WVTR values above 2000 g/m²/24 hrs when stretched at the higher stretch ratios.

At the 100 percent elongation cycle test, the highly elastic skin layers did not effectively overcome the poorer elastic properties of the core layer. At this high elongation level the filled metallocene plastomer core layer appeared to be beyond its elastic region and did not demonstrate much retraction. The skin layers, at less than 5 percent by volume of the total film thickness, could not compensate for the core's lack of elasticity at that level of elongation.

The addition of 10 percent Kraton® to the filled metallocene catalyzed polyethylene formulation (106E) improved elastic properties, but the WVTR was lower than that of the 106A formulation without the Kraton®. When the two monolayer control films were stretched to higher ratios (5.0–5.5x), the WVTR and elastic properties at 50 percent seemed to converge and become similar. At that high stretch ratio, the metallocene catalyzed polyethylene resin may have been stretched beyond its elastic region. At high stretch/strain levels, these elastic materials may undergo a hardening and become more like a non-elastic plastic material. Their recovery ability becomes minimal. This appears to be the case with the metallocene-catalyzed polyethylene films stretched to the high stretch ratios.

The Pebax® and Pellethane® skin layer films demonstrated high performance for elasticity (lowest hysteresis), but the WVTR was significantly reduced. Although these films were laminated in such a way to demonstrate biaxial stretch, they were limited in the machine direction. The highest level of elongation in the MD from these laminates was 26 percent. It was therefore not possible to test the films at 100 percent elongation in the MD. Even at 50 percent, very high tensions and some tearing and film/spunbond delamination were evident. The MD retraction was, however, improved with the addition of the skin layer.

The film with the Pebax® 2533 blended skin layer with the 106E core layer would exhibit the best overall elastic properties based on all of the previously mentioned data, if an optimum formulation was chosen. This can be concluded based upon the results of a test of the individual properties of the Pebax 2533 versus the Pellethane 2103-80 in Table 8.

TABLE 8

| Polymer | Ext. Tension/Retr. Tension | Hysteresis | WVTR |
| --- | --- | --- | --- |
| Pebax ® 2533 @ 10 gsm | 190/140 | 27% | 2800 |
| Pellethane ® 2103-80AE @ 10 gsm | 290/150 | 48% | 2200 |

Incompatibility of materials compounded or coextruded together was a concern in developing the multilayer materials. Pebax®, Pellethane® and Estane® are all polar materials, unlike the non-polar polyethylene core layer and the polypropylene spunbond layer. EMA or Kraton® materials were successfully blended with the skin layer to act as compatibilizers and improve adhesion to the core layer and the spunbond. It is surmised that compounding and coextrusion were successful because of the thorough blending of the skin materials and adhesion of the skin to core layers.

Filled elastomeric films having improved elastic efficiency are therefore described from monolithic thin coextruded skin layers encapsulating a filled core layer. The addition of a very thin skin layer comprising a non-filled elastic or blend of elastic polymers during film coextrusion on either one or both sides of the filled core material will improve the retraction and reduce the set of the product film at up to 50 percent elongation. At higher than 50 percent elongation it was found that the tested materials experienced lower retraction. The skin layer, however, must be sufficiently thin to allow the moisture to continue to pass through. The skin layers can be similar on both sides as in an A-B-A coextruded structure or different on either side as in an A-B-C structure, where B is the filled core layer and A and C are the skin layers.

While the invention has been described in detail with particular reference to a preferred embodiment thereof, it should be understood that many modifications, additions, and deletions can be made thereto without departure from the spirit and scope of the invention as set forth in the following claims.

What is claimed is:

1. A breathable, elastic multilayered film comprising:
   a core layer comprising a first elastomer, at least one filler, and a high performance elastomer, wherein said first elastomer is a low performance elastomer present in an amount of between about 35 and 50 percent of said core layer; and
   at least one skin layer comprising a second elastomer, wherein said second elastomer is a high performance elastomer, and further, wherein said elastic multilayered film demonstrates a water vapor transmission rate of greater than 1000 g/m²/24 hrs.

2. The breathable, elastic multilayered film of claim 1 wherein said second elastomer has a hysteresis value less than 60 percent.

3. The breathable, elastic multilayered film of claim 1 wherein said first elastomer comprises a polyolefin and said second elastomer is selected from the group consisting of thermoplastic polyurethanes, polyetheramides, and block copolymers, and combinations thereof.

4. The breathable, elastic multilayered film of claim 3 wherein said film includes two skin layers on opposing sides of said core layer.

5. The breathable, elastic multilayered film of claim 3 wherein said skin layer(s) further include an ethylene methyl acrylate.

6. The breathable, elastic multilayered film of claim 3 wherein said first elastomer is a polyethylene.

7. The breathable, elastic multilayered film of claim 3 wherein said skin layer(s) include a compatibilizer.

8. The breathable, elastic multilayered film of claim 3 wherein an antiblocking agent is blended in the skin layer(s).

9. The breathable, elastic multilayered film of claim 3 wherein the film has a thickness of between about 0.6 and 1.2 millimeters, with the skin layer(s) having a total thickness of about 3 percent of the total film thickness.

10. A breathable laminate material comprising:
   an elastic multilayered film comprising a core layer of a first elastomer, at least one filler and a high performance elastomer, wherein said first elastomer is a low performance elastomer present in an amount of between about 35 and 50 percent of said core layer, and said film having at least one skin layer of a second elastomer; and further, wherein said first elastomer is a polyolefin and said second elastomer is selected from the group consisting of thermoplastic polyurethanes, polyetheramides, block copolymers, and combinations thereof; and at least one support layer bonded to said multilayered film.

11. A personal care absorbent article including the breathable laminate material of claim 10.

* * * * *